(12) United States Patent
Wolffgramm

(10) Patent No.: US 7,632,826 B2
(45) Date of Patent: Dec. 15, 2009

(54) USE OF AGONISTS OF THE GLUCOCORTICOSTEROID AND/OR MINERALO-CORTICOSTEROID RECEPTORS, IN PARTICULAR CORTICOSTEROIDS FOR THE TREATMENT OF ADDICTION

(75) Inventor: Jochen Wolffgramm, Berlin (DE)

(73) Assignee: Curamentis Ltd., Nottingham (GB)

( * ) Notice: Subject to any disclaimer, the term of this patent is extended or adjusted under 35 U.S.C. 154(b) by 9 days.

(21) Appl. No.: 11/148,874

(22) Filed: Jun. 8, 2005

(65) Prior Publication Data

US 2005/0222112 A1    Oct. 6, 2005

Related U.S. Application Data

(60) Division of application No. 09/851,817, filed on May 9, 2001, now abandoned, which is a continuation of application No. PCT/EP99/08598, filed on Nov. 9, 1999.

(30) Foreign Application Priority Data

Nov. 10, 1998 (EP) .................. 98121338

(51) Int. Cl.
    A61K 31/573   (2006.01)
    C07J 5/00     (2006.01)
(52) U.S. Cl. ........................ 514/179; 552/574; 552/576; 552/577
(58) Field of Classification Search .................. 514/179
    See application file for complete search history.

(56) References Cited

FOREIGN PATENT DOCUMENTS

WO   WO 97/03677   2/1997
WO   WO 98/42275   10/1998

OTHER PUBLICATIONS

Mantsch et al., "Corticosterone Facilitates the Acquisition of Cocaine Self-Administration in Rats: Opposite Effects of the Type II Glucocorticoid Receptor Agonist Dexamethasone" The Journal of Pharmacology and Experimental Therapeutics (1998) vol. 287, No. 1, pp. 72-80.*
Montgomery, S° P. and Dafny, N. Cyclophosphamide and cortisol reduce the severity of morphine withdrawal. Int. J. Immunopharmacol. (1987) vol. 9, pp. 453-457.*
Capasso, A. et al. "Dexamethasone pretreatment redu~s the psychomotor stimulant effects induced by cocaine and amphetamine in mice" Prog. Neuropsvchopharmacol. & Biol. Psychiat. (1995) vol. 19, pp. 1063-1079.*
Albrecht, K., et al., "Diagnostik und Therapie von akuten Drogennotfallen," Z. arztt Fortbild., 85:701-707 (1992).
Capasso, A. et al., "Dexamethasone pretreatment reduces the psychomotor stimulant effects induced by cocaine and amphetamine in mice," Prog. Neuro-psychopharmacol. & Biol. Psychiat., 19:1063-1079 (1995).
Capasso, A. et al., "Dexamethasone selective inhibition of acute opioid physical dependence in isolated tissues," J. Pharmacot Exp. Therapeut., 276:743-751(1996).
Capasso, A. et al., "Dexamethasone inhibition of acute opioid physical dependence in vitro is reverted by anti-lipocortin-1 and mimicked by anti-type II extracellular PLA2 antibodies," Life Sci., 61:127-134 (1997).
Ehrenreich, H. et al., "OLITA: an alternative in the treatment of therapy-resistant chronic alcoholics," Eur. Arch Psychiatry Clin. Neurosci., 247:51-54(1997).
Mantsch, J.R. et al., "Corticosterone facilitates the acquisition of cocaine self-administration in rats: opposite effects of the type ll glucocorticoid receptor agonist dexamethasone," J. Pharmacol. Exp. Therapeut, 287:72-80 (1998).
Montgomery, S.P., et al. "Cyclophosphamide and cortisol reduce the severity of morphine withdrawal" Int J. Immunopharmacol., 9:453-457 (1987).
Reddy, D.S., et al., "Neurosteroid coadministration prevents development of tolerance and augments recovery from benzodiazepine withdrawal anxiety and hyperactivity in mice," Methods Find Exp Clin Pharmacol, 19:395-405 (1997).
Sass, H. et al. "Relapse prevention by acamprosate. Results from a placebo-controlled study on alcohol dependence," Arch. Gen. Psychiatry, 53:673-680 (1996).
Sze, P.Y., "The permissive role of glucocorticoids in the development of ethanol dependence and tolerance," J. Drug Alcohol Dep., 2:381-396 (1977).
Whitworth, A.B. et al., "Comparison of acamprosate and placebo in longterm treatment of alcohol dependence," Lancet, 347:1438-1442 (1996).
Caggiula et al., "The role of corticosteroids in nicotine's physiological and behavioral effects," Psychoneuroendocrinology, 22:143-159 (1998).
Hardman et al., Goodman & Gilman's the Pharmacological Basis of Therapeutics, 9th Ed., p. 51 (1996).
Brecht, J. G., et al., "Alcoholism:The cost of illness in the Federal Republic of Germany" PharmacoEconomics, 10:484-493 (1996).
Heyne, A.,"The development of opiate addiction in the rat," PharmacoL Biochem. Behav., 53:11-25 (1996).
Roch, I., et al., "Empirische Ergebnisse zum Therapieabbruch bei Drogenabhangigen: ein. LiteraturUberblick," Sucht, 38:305-322 (1992).
Schmidt, L.G., et al., "Relapse Prevention in alcoholics with an anticraving drug treatment: first results of the Berlin study,". Pharmacopsychiatry, 27:21-23 (1996).
Sobell, L.C., et al., "What triggers the resolution of alcohol problems without treatment?" Alcohol. Clin. Exp. Res., 17:217-224 (1993).
Süss. H. M., "Zur Wirksamkeit der Therapie bei Alkoholabhangigen: Ergebnisse einer Meta-Analyse,".Psychol Rundschau, 46:248-266 (1995).
Wolffgramm, J., "Abhangigkeitsentwicklung in Tiermodell," Z. Klin. Psychol., 24:107-117 (1995).
Wolffgramm, J., et al., "From controlled drug intake to loss of control: the irreversible development of drug addiction in the rat," Behav. Brain Res., 70:77-94 (1995).

* cited by examiner

Primary Examiner—Shaojia Anna Jiang
Assistant Examiner—Eric S Olson
(74) Attorney, Agent, or Firm—Ropes & Gray LLP; James F. Haley, Jr.; Karen Mangasarian

(57) ABSTRACT

Corticosteroid receptors and/or mineralo-corticoid receptors are administered in combination with an addictive drug or the pharmacodynamic equivalent thereof for the therapy of an addictive disease triggered by said addictive drug or connected thereto.

3 Claims, No Drawings

USE OF AGONISTS OF THE GLUCOCORTICOSTEROID AND/OR MINERALO-CORTICOSTEROID RECEPTORS, IN PARTICULAR CORTICOSTEROIDS FOR THE TREATMENT OF ADDICTION

This application is a divisional of U.S. application Ser. No. 09/851,817, filed May 9, 2001, now abandoned, which is a continuation of International Application PCT/EP99/08598, filed Nov. 9, 1999, designating the U.S., which in turn claims priority under 35 U.S.C. § 119 to European Patent Application 98 12 1338.2, filed Nov. 10, 1998.

BACKGROUND OF THE INVENTION

The present invention relates to the use of agonists of the glucocorticosteroid and/or mineralo-corticosteroid receptors, in particular corticosteroids, for the treatment of addictive diseases, a pharmaceutical preparation for the treatment of addictions and a method for the treatment of addictions.

Alcohol and drug addiction have been considered non-curable up to now. All therapy programs, even the new approaches of an "anti-craving" pharmacotherapy, could only support the addicted patient in his will not to have a relapse after withdrawal but they cannot reverse the core of the disease—the latent loss of control over taking of drugs. This is why the risk of a relapse is still high many years after withdrawal.

Alcohol and drug addiction (often called "dependency") is a psychological disease with a compulsively increased self-administration of the addictive drug. The addicted consumer is not able to regulate his intake of drugs, to adjust it to his currently prevalent conditions (e.g. the present social situation) and to take alternative behaviour into consideration (American Psychiatric Association, 1994). The "loss of control", once started, disappears only extremely slowly; even more, it seems to be spontaneously irreversible in many cases (Sobell et al., 1993). This "loss of reversibility" becomes statistically clear when looking at the extremely high percentage of relapses even after long periods of abstinence. In follow-up studies after detoxification and subsequent therapy of alcohol addicts, only a quarter up to a third, at the most, of the addicted patients remained abstinent permanently (Süβ, 1995; Veltrup et al., 1995). Spontaneous recovery success and higher percentages of long-term abstinent patients are usually due to the fact that—due to the inclusion criteria of the relevant study—not only clearly addicted patients but also "problem drinkers", i.e. patients with excessive but still controlled alcohol consumption, were included in the study (compare Stetter and Axmann-Kremar, 1996; Wieser and Kunad, 1965). For other drugs (opiates, cocaine, amphetamine derivatives), less reliable follow-up data are available. Usually, one starts out from an even worse cure prognosis for opiate addiction than for alcohol addiction (compare Roch et al., 1992).

A comparison of different therapy approaches and treatment factors (compare Küfner, 1997) is difficult due to the fact that different therapy institutions and programs differ not only in their secondary-conditions (inclusion criteria, open and closed therapy, duration of treatment, duration of aftercare, termination criteria, documentation etc.) but also in the fact that their therapy criterion is not defined in a uniform way. The margin ranges from total abstinence to a more-or-less abstinence with few, tolerated relapses to a moderate, controlled intake of substances. If the latter was possible to a larger. extent, this would be the step back from loss of control to controlled consume. This, however, is only rarely the case. Rist (1996) refers to a meta-analysis with regard to alcoholism therapies by Süβ (1995) and the "VDR" study (Küfner and Feuerlein, 1989) according to which the percentage of non-permanently abstinent but improved patients is comparatively low. According to this, a latent addict has basically only the choice between a relapse into addiction and a continuation of abstinence while fighting the relapse all the time.

Standard forms of therapy support the patient in this fight, at the most. Since the cause for a relapse often depends on the circumstances, the main aim of many psychological and behavioural therapy approaches is the psychological and social consolidation of the patient. Also important are teaching and information, which aim at the addict being able to deal with his disease in a competent way, and, partly, specific training to cope ('coping skills', Rist, 1996). Conditioning and aversion progammes aim at breaking set patterns (stimulus reaction relationships connected with the taking of the substance) and/or at forming new, aversive associations with drinking alcohol and taking drugs.

Medical treatment usually is given in addition to psychotherapy or a behavioural therapy, however, partly it is also given without taking any other additional measures. Generally three fields of application can be differentiated: (a) substitution treatment, (b) anti-reward therapies and (c) anti-craving therapies. Substitution treatment was introduced in an opiate addicts years ago (Finkbeiner et al., 1996; Bühringer et al., 1997). Instead of the addictive drug (mostly heroin) the pharmacodynamically similar substitution substance (mostly methadone) is taken by the addict. This concept does not represent an addiction 'therapy' since craving for the original drug returns after (gradual) discontinuing with the substitute, often, also, the craving is still present during substitution in a latent way. The benefit of substitution lies more in social factors (re-integration of the addict), decriminalisation of the drug scene and reduction of morbidity and mortality.

Anti-reward-treatments with pharmaceuticals used to be similar to the aversion strategy (example: disulfiram-treatment of alcoholism). This approach was controversial in Europe for a long time but has had a revival recently (OLITA and ALITA program: Ehrenreich et al., 1997). In comparison to conventional therapy programmes the OLITA/ALITA concept is different due to an intensive ambulant long-term treatment (for two years the alcoholics patients are called in for counselling and administration of acetaldeyd-dehydrogenase-inhibiting substances for induction of an intolerance towards alcohol at the same time). The authors of the study report about a therapy success comprising approximately 50% of the patients (lasting abstinence); thus the treatment program would be more successful than standard approaches in therapy. Long-term follow-up studies, however, have not yet been carried out. A rather great, multi-center study is currently in the planning phase (oral communication).

At present, hopes are put on a medium-term blockage of the central nervous opioidergic transmission by means of the opioid-antagonists naltrexone. The addict who had previously been treated with naltrexone does not feel any effect when an opiate is administered, thus there is no rewarding effect either. This reduces the risk of relapse. The problem remains the patient's compliance, i.e. his willingness to accept the medication. Thus, the usefulness of a naltrexone therapy is controversial. Within a short- or medium-term period a naltrexone therapy seems to be effective, i.e. it can reduce the number of relapses and also have a favourable influence on the severity. This is particularly true for the treatment of alcoholics (Mann and Mundle, 1996). Lasting effects beyond the end of the pharmaceutic therapy have not yet been described.

According to definition, anti-craving medication is supposed to reduce the addict's obsessive need for his addictive drug ("craving"). There is an enormous amount of such approaches which cannot be categorised as to a common principle. The above-mentioned naltrexone-therapy, for example, is also used as an anti-craving strategy despite the fact that, with view to pharmacology, it is, probably more based on a blockage of effectiveness rather than on influencing motivation. In principle, the effects and the modes of action of the putative anti-craving drug therapy seem to be heterologous. A survey by Soyka (1997) mentions glutamate modulators, glutamate antagonists, opiate antagonists, dopamine agonists, dopamine antagonists, serotonin re-uptake inhibitors, serotonin antagonists and MAO inhibitors. Apart from the above-mentioned naltrexone with which a positive effect is likely, only the glutamate modulator acamprosate has proven to be effective in clinical tests carried out in various centres across Europe. In the German part of the study (Sass et al., 1996), at the end of the study 42% of the patients of the verum group were still abstinent after 48 weeks of treatment, in the placebo group there were only 20%. In Austria, the respective results were 30% of the acamprosate-treated patients and 21% of the placebo group (Wirtworth et al.,, 1996). There are no statistically significant data on long-term effects after discontinuing with the pharmaceutical preparation available yet. Looking at all the studies together, acamprosate about doubles the prospect—at least during the period of treatment—to remain abstinent after approximately one year of treatment. This is a success not to be underestimated. However, it remains to be said that despite acamprosate treatment approximately 70% of the addicted patients, on average in Europe, did not achieve the therapy aim of permanent abstinence (with placebo treatment there were 85%). Thus, even the up to now most effective therapeutic preparation for the treatment of addiction can be used successfully only with a small number of addicts.

The great portion of therapy failures of 60 to 90% shows that the forms of psycho, behaviour and drug therapy established today can cure the addictive disease either not at all or only insufficiently. Moreover, it has to be considered that many of the patients who stay abstinent have to fight the thought of relapse daily and organise themselves in self-help groups, such as the Alcoholics Anonymous, to support each other in their confrontation with the latent addiction (compare Schwoon, 1996). The number of those addicted patients really cured, i.e. freed from their loss of control is, thus, likely to be even lower than the figures of relapse statistics.

SUMMARY OF THE INVENTION

It is desirable to name a method of treatment, wherein the loss of control can be reversed so that the previously addicted patient finds himself in the status quo ante. In order to achieve this aim, the task of the present invention was to name substances which make medical treatment of an addictive disease possible. The medical drugs should be useable in a therapy with a causal effect.

This task has been solved by the use of agonists of the glucocorticosteroid and/or mineralo-corticosteroid receptors, particularly corticosteroids, and an addictive drug or a pharmacodynamic equivalent thereof for the production of a pharmaceutical preparation for therapy of an addictive disease caused by or connected with the addictive drug. The addictive drug can, for example, be an opiate or the drug the patient is addicted to.

Further, as state of the art to be mentioned are: MONTGOMERY, STEPHEN P. ET AL, Cyclophosphamide and cortisol reduce the severity of morphine withdrawal, INT. J. INMUNOPHARMACOL. (1987), 9(4), 453-7, CAPASSO, A. ET AL: 'Dexametbasone selective inhibition of acute opioid physical dependence in isolated tissue, PHARMACOL. EXP. THER. (1996), 276 SZE, PAUL Y.: The permissive role of 1-3 glucocorticoids in the development of ethanol dependence and tolerance, DRUG ALCOHOL DEPEND. (1977), 2(5-6), 381-96, CAPASSO, ANNA ET AL: Dexamethasone 1-3 pretreatment reduces the psychomotor stimulant effects induced by cocaine and amphetamine in mice, PROG. NEURO-PSYCHOPHARMACOL. BIOL. PSYCHIATRY (1995), 19(6), 1063-79, ALBRECHT K. ET AL: Diagnosis and therapy of acute drug emergencies, DIAGNOSTIK UNO THERAPIE VON AKUTEN DROGENNOTFÄLLEN, ZEITSCHRIFT FÜR ÄRZTLICHE FORTBILDUNG, (1992) 86/14 (701-707), MANTSCH J R ET AL: Corticosterone facilitates the acquisition of cocaine self-administration in rats: opposite effects of the type II glucocorticoid receptor agonist dexamethasone., JOURNAL OF PHARMACOLOGY AND EXPERIMENTAL THERAPEUTICS, (1998 October) 287 (1) 72-80, CAPASSO, ANNA ET AL: Dexamethasone 1-3 inhibition of acute opioid physical dependence in vitro is reverted by anti-lipocortin-1 and mimicked by anti-type II extracellular PLA2 antibodies, LIFE SCI. (1997), 61(10), PL127-PL134, REDDY, D. 5. ET AL: Neurosteroid 1-3 coadministration prevents development of tolerance and augments recovery from benzodiazepine withdrawal anxiety and hyperactivity in mice, METHODS FIND. EXP. CLIN. PHARMACOL. (1997), 19(6), 395-405 as well as WO-A-97 03677.

None of the works discloses the curing of the addiction or a lasting therapy of a manifested addiction. In some of the publications, acute effects, tolerance development, physical dependency and withdrawal symptoms as a consequence of drug intake are described. Apparently, corticoids seem to have an effect on these, i.a. The aim of a therapy can, however, not be the treatment of withdrawal but only the therapy of a manifested disease, i.e. of a psychological dependency. Withdrawal, i.e. a detoxification of the patient physically dependent on the addictive drug, should take place before the treatment of the addiction per se. For such detoxification various medical drugs are used, possibly also corticosteroids which, however, do not serve the purpose of treating the addiction.

The treatment of the psychological dependency (i.e. the addiction) is carried out preferably on the already detoxified patient; it is supposed to free him from his uncontrollable urge for addictive drugs. None of the publications deals with curing the psychological dependency.

The treatment of an addiction with a corticosteroid as mono-substance does not lead to complete recovery. What is crucial is the combination with the simultaneously/subsequently administered addictive drug. None of the mentioned publications uses such combination to achieve a lasting, causal therapy target. In none of the studies were the addicted patients or experimental animals subjected to combination treatment.

In detail, the following is to be said with regard to the publications by Montgomery & Dafny, 1987, Capasso et al., 1996, Capasso et al., 1997, Reddy & Kulkarni,. 1997:

The studies presented in the above publications relate to the effects of corticosteroids on tolerance development, physical dependency and withdrawal symptoms as a consequence of drug-taking. A withdrawal-reducing effect of corticosteroids i.a. is described. Medication accompanying the withdrawal with the aim of reducing the withdrawal symptoms is not the purpose of the drug therapy suggested according to the invention. The latter only starts after the withdrawal symptoms have worn off and pursues the aim to cure the addict from his urge for addictive drugs and from loss of control. It has to be stressed that physical dependency (which leads to the withdrawal syndrome) and psychological dependency (addiction) are completely different.

Using experimental animals who, after an operation, were not able to form corticosteroids naturally-occurring in the body, Sze, 1997 describes the participation of these hormones in the development of tolerance against and physical dependency on alcohol. This happened by means of substitution of the corticoid hormones which were not present in the body by introduction of said hormones from outside. The study has nothing to do with addiction (e.g. no voluntary but a forced supply of alcohol took place), it shows—similar to the above-mentioned publications—that corticosteroids play a role in the development of tolerance, physical dependency and withdrawal symptoms.

Capasso et al., 1995, show that specific corticosteroids can reduce the acute psycho-stimulating effects of cocaine and amphetamines. This effect may possibly play a certain role in the preventive area (i.e. during cocaine or amphetamine abuse) but it is not at all related to an addiction therapy on a patient who has already been through withdrawal and is to be freed from his psychological drug dependence. Furthermore, as in all the other studies, too, we here deal with the effects of a corticosteroid mono-substance and not with the combination with the addictive drug according to the invention. Only such a combination is successful.

Albrecht & Lampe, 1992, describe medical emergency measures after acute poisoning with addictive drugs. According to classic indication (particularly for immunosuppression) also corticosteroids are used. The treatment with corticosteroids does not serve the function of an addiction therapy nor is it used in combination with the addictive drug. Rather, it corresponds to the standard therapeutic use of these classes of substances.

Mantsch et al., 1998, show that some corticosteroids facilitate the learning of a cocaine self-administration task in rats, others rather block it. similar to the above-cited study by Capasso et al., 1995, the effects of taking an addictive drug (in the former: on the motoric effects, here: on the self-administration) are modulated by the corticosteroid. Thus, one of many corticosteroid effects is described. This effect has nothing to do with the combination therapy of an addiction on a post-withdrawal patient according to the invention. According to the invention, the corticosteroid is used as a sensitizing agent of a moulding process.

WO-A-97/03677 relates to the inhibition of a sub-class of glutamate receptors (NMDA receptors) described by means of pregnenolone sulfate derivatives. The method is considered to be useable also with acute withdrawal syndrome. It is known that some withdrawal symptoms are mediated via NMDA receptors of the brain. According to the invention the withdrawal is not facilitated but causal therapy of the addiction takes place. Moreover, according to the invention, antagonists of the NMDA receptor are not used but agonists of the corticosteroid receptors in connection with the addictive drug administered in a particularly forced manner.

In animal experiments based on the established animal model of addiction (review article: Wolffgramm and Heyne, 1995) it was found that administration of corticosteroids can change addictive behaviour successfully, if the administration of corticosteroids is combined with a preferably highly-dosed administration of an addictive drug or a pharmacodynamic equivalent thereof independent from the addictive individual's wish as to the intake. In this context, the addictive drug or the pharmacodynamic equivalent thereof can be administered simultaneously or sequentially with the administration of corticosteroids. The animal model (rat) used for the analysis of the therapy is known to the international world of experts in the field and allows for an analysis of addiction development as well as testing of new approaches in therapy.

After several months of taking the substance (alcohol, opiate, amphetamine, etc.) voluntarily (no animal is forced to take the addictive drug), some rats develop an addiction spontaneously. They lose control over the taking of the drug and, for example, also drink denatured drug solutions which non-addicted animals always avoid. Probably, there are no intermediary conditions between addiction and non-addiction; this has been proven in the animal model, at least for opiate and amphetamine addiction. After forced administration of addictive drugs—an addictive drug-containing solution served as the only source of drinking solution—a physical dependency developed (withdrawal syndrome) but no loss of control, i.e. no addiction.

DETAILED DESCRIPTION OF THE INVENTION

Surprisingly it was found that with administration of agonists of the glucocorticosteroid and/or mineralcorticosteroid receptors, in particular corticosteroids, in a certain sequence to the forced administration of an addictive drug or the pharmacodynamic equivalent thereof, the development of addiction is set back to the condition before the addiction. If the condition of an addiction has occurred, neither the administration of an agonist of the glucocorticosteroid and/or mineralo-corticosteroid receptors by itself, particularly corticosteroid, nor the forced intake of the addictive drug or the pharmacodynamic equivalent thereof by itself is suitable for reversing the condition again. A simultaneous or successive combination of the agonist of the glucocorticosteroid and/or mineralo-corticosteroid receptors, particularly corticosteroid, and the addictive drug administered in a forced way or the pharmacodynamic equivalent thereof can take the addictive patient back into a condition corresponding to the one before the addiction. In this context, the agonist of the glucocorticosteroid and/or mineralo-corticosteroid receptors, particularly the corticosteroid, seems to have a preparatory or synchronising role ("ready to imprint" or "imprint now!"), while the highly-dosed administration of the addictive drug or the equivalent thereof eliminates the associations present up to now, replaces them by new ones and, thus, deletes the existing "addiction memory".

As agonist of the glucocorticosteroid and/or mineralo-corticosteroid receptors, particularly corticosteroids, according to the invention, can be used the corticoid hormones occurring naturally in the body, e.g. corticosterone, cortisone, particularly as cortisone acetate, or other physiological derivatives, as well as cortisol. Synthetic compounds, such as prednisolone, prednisone, prednyliden, methylprednisolone, triyamcinolone, betamethasone, dexamethasone, parametha-sone, fluocortolone, deflazacort, cloprednoe and fludrocorti-sone or combinations thereof can also be used. In the group of the natural corticoid hormones cortisol and cortisone are preferably used, since there is vast experience with administration in humans. For substitution treatment, generally, corticoid hormones are used which not only exhibit the affinity to glucocorticoid receptors (GR) but also to mineral corticoid receptors (MR). If one of the mentioned preparations is a pure GR agonist, such as betamethason, it is possibly advantageous to additionally administer an MR-effective mineral corticoid, such as fludrocortisone. Fludrocortisone could also be used as monosubstance effectively, since it exerts glucocorticoid effects.

According to the invention, any substance-related addictive diseases can be treated. The part of the agonists of the glucocorticosteroid and/or mineralo-corticosteroid receptors in therapy always remains the same. The second part is represented by an addictive drug administered in a forced way or the pharmacodynamic equivalent thereof. Preferably, either the addictive drug the patient is addicted on, or an opiate should be administered. Accordingly, apart from an opiate dependency, also nicotine addiction (smoking tobacco), cannabinoid dependency (hashish, marihuana), psychostimulants and entactogen dependency, cocaine addiction inclusive "crack" and alcoholism as well as polyximanic addictions can be cured using the so-called therapy forms. In the latter three cases, optionally, medical side effect would have to be seen to which would be connected to a highly-dosed forced administration of an addictive drug or the equivalent thereof possibly over several weeks. The combination of an administration of the agonist of the glucocorticosteroid and/or mineralo-corticosteroid receptors, particularly corticosteroid, and an addictive drug or the pharmacodynamic equivalent thereof is important according to the invention. The administration of the agonist of the glucocorticosteroid and/or mineralo-corticosteroid receptors, particularly corticosteroid, has to take place before and/or during the forced administration of the addictive drug. Both substances are used in high dosages which are not deleterious to health. There are the following possibilities, while the duration of administration per phase is between some days to some weeks each:

administration of both the agonist of the glucocorticosteroid and/or mineralo-corticosteroid receptors, particularly corticosteroid, and an addictive drug or the equivalent thereof, first, the administration of the agonist of the glucocorticosteroid and/or mineralo-corticosteroid receptors, particularly the corticosteroid, immediately followed by the forced administration of an addictive drug or the equivalent thereof, first, the administration of both the agonist of the glucocorticosteroid and/or mineralo-corticosteroid receptors, particularly corticosteroid, immediately followed by the administration both of corticosteroid and an addictive drug or the pharmacodynamic equivalent thereof, first, the administration of both the agonist of the glucocorticosteroid and/or mineralo-corticosteroid receptors, particularly corticosteroid and addictive drug or the pharmacodynamic equivalent thereof, immediately followed by the forced administration both of corticosteroid and an addictive drug or the pharmacodynamic equivalent thereof, without agonist of the glucocorticosteroid and/or mineralo-corticosteroid receptors, particularly corticosteroid, first, the administration of the agonist of the glucocorticosteroid and/or mineralo-corticosteroid receptors, particularly of the corticosteroid, immediately followed by the administration of the addictive drug (or the pharmacodynamic equivalent thereof) and agonists of the glucocorticosteroid and/or mineralo-corticosteroid receptors, particularly corticosteroid, followed by the forced administration of the addictive drug or the pharmacodynamic equivalent thereof without administration of the agonist of the glucocorticosteroid and/or mineralo-corticosteroid receptors, particularly of the corticosteroid.

Apart from the administration of a single agonist of the glucocorticosteroid and/or mineralo-corticosteroid receptors, particularly a corticosteroid, the administration of combinations of various agonists of the glucocorticosteroid and/or mineralo-corticosteroid receptors, particularly corticosteroids, is also possible. In the case of polytoxicomania (dependency on several drug at the same time) both a simultaneous and a sequential treatment would be possible. Since a sequential therapy would create risks and, also, a loss of effectiveness might occur in simultaneous re-programming, a single therapy approach seems advantageous. In this case, either the main drug could possibly be used in combination with secondary substances often used for forced administration or a forced administration of opiate could take place.

Combinations of agonists of the glucocorticosteroid and/or mineralo-corticosteroid receptors, particularly corticosteroid, and addictive drug or the pharmacodynamic equivalent thereof means, according to the invention, that either one or more agonists of the glucocorticosteroid and/or mineralo-corticosteroid receptors, particularly corticosteroid(s), are mixed with an addictive drug or the pharmacodynamic equivalent thereof in a standard pharmaceutical formulation and are, thus, given to the addict simultaneously. It is, however, also possible to formulate the substances separately from each other e.g. in galenic preparations, and to give them to the patient separately from each other. This has, for example, the advantage that the addictive drugs can be administered orally and the agonists of the glucocorticosteroid and/or mineralo-corticosteroid receptors, particularly corticosteroids, can be administered parenterally. If, however, an oral or other administration is possible for both components of the pharmaceutical preparation according to the invention, it can be advantageous to administer the components in one formulation each.

If in the treatment of the addiction a two-phase-treatment is desired, wherein, to start with, the agonist of the glucocorticosteroid and/or mineralo-corticosteroid receptors, particularly the corticosteroid is administered, followed by a combination of agonists of the glucocorticosteroid and/or mineralo-corticosteroid receptors, particularly corticosteroid, the addictive drug or the pharmacodynamic equivalent thereof, it can be an advantage to carry out the administration in such a way that, for example, one form of administration, e.g. blister pack, contains an amount of formulations containing agonists of the glucocorticosteroid and/or mineralo-corticosteroid receptors, particularly corticosteroid, for example tablets or suppositories, which is sufficient, initially, for the first phase, followed by a corresponding amount of tablets containing the combination of agonists of the glucocorticosteroid and/or mineralo-corticosteroid receptors, particularly corticosteroid, and addictive drug or pharmacodynamic equivalent thereof. Then, optionally, a corresponding amount of the addictive drug-containing formulations can be present if a three-phase-treatment is necessary. This configuration of a formulation represents an example of a suitable administration form for the. administration of the pharmaceutical preparation according to the invention. Modifications of the configurations described can be made by the person skilled in the art and are adjustable to the relevant situation as to treatment.

The dosage of the agonists of the glucocorticosteroid and/or mineralo-corticosteroid receptors, particularly corticosteroids, to be used and of an addictive drug or the pharmacodynamic equivalent thereof, are to be adjusted to the patient, individually, in particular, an deleterious overdosage has to be avoided. How the dosage can be determined for a patient individually is known to the therapist. In principle, according to the invention, there is a differentiation between the administration of a initial dosage at the beginning of the therapy and maintenance dosage during continuation of the therapy after administration of the initial dosage of the relevant agonist of the glucocorticosteroid and/or mineralo-corticosteroid receptors, particularly corticosteroid. In this context, the dosage of the agonist of the glucocorticosteroid and/or mineralo-corticosteroid receptors, particularly corticosteroid, will be high (initial dosage) at the beginning and will be reduced to a maintenance dosage. For the various agonists of the glucocorticosteroid and/or mineralo-corticosteroid receptors, particularly corticosteroids, the first dosage varies according to the "Cushing threshold" which, if passed, causes a typical syndrome of undesired side effects or accessory symptoms. The following table shows estimates of dosage guidelines for a patient having 60 to 80 kg.

| substance | maintenance dosage | initial dosage (in multiplication of the maintenance dosage) |
|---|---|---|
| glucocorticoidhormones occurring naturally in the body: | | |
| cortisol (hydrocortisone) | 30-50 mg/day | ×3 |
| cortisone acetate | 40-60 mg/day | ×2 |
| corticosterone | 30-50 mg/day | ×2 |
| synthetic glucocorticoids: | | |
| prednisolone | 8-12 mg/day | ×8 |
| prednisone | 8-12 mg/day | ×8 |
| prednylidene | 8-12 mg/day | ×8 |
| methylprednisolone | 8-12 mg/day | ×5 |
| triamcinolone | 6-9 mg/day | ×6 |
| betamethasone | 1-2 mg/day | ×2 |
| dexamethasone | 2-3 mg/day | ×5 |
| paramethasone | 3-5 mg/day | ×3 |
| fluocortolone | 10-15 mg/day | ×8 |
| deflazacort | 10-15 mg/day | ×6 |
| cloprednol | 8-12 mg/day | ×5 |
| synthetic mineralo-corticoid (possibly as additive) | | |
| fludrocortisone | 0.2-0.3 mg/day | ×2 |

The dosages with the forced administration (independent from the patient's wish) of the addictive drug or the pharmacodynamic equivalent thereof depends on the highest dosage possible where no severe side effects, possibly deleterious to health, of a chronic administration are to be expected. The occurrence of the latter can crucially depend on the health condition the patient is in at the beginning of the therapy (e.g. liver function, drug tolerance, etc.). With the administration of opiate, for example, respiratory depression has to be expected. Once tolerance (insensitivity) has developed against this effect, an increase of the dosage is possible. In substitution for other drugs, some guidelines are given for dosage of opiates (corresponding values e.g. of nicotine or tetrahydrocannabinol depend on the relevant dosage thresholds of the undesired side effects):

| | |
|---|---|
| morphine-retard | 30-60 mg/day |
| codeine | 30-60 mg/day |
| dihydrocodeine | 60-120 mg/day |
| levomethadone | 5-15 mg/day |
| tilidin | 50-100 mg/day |

The method of the invention for the treatment of addictive diseases is characterised by the administration of at least one agonist of the glucocorticosteroid and/or mineralo-corticosteroid receptors, particularly corticosteroid, and an addictive drug or the pharmacodynamic equivalent thereof. In this context, the administration of the agonist of the glucocorticosteroid and/or mineralo-corticosteroid receptors, particularly corticosteroid, takes place before and/or during the forced administration of the relevant addictive drug or the pharmacodynamic equivalent thereof. As described above, there are five possibilities:

1. Agonist of the glucocorticosteroid and/or mineralo-corticosteroid receptors, particularly corticosteroid>combination of agonist of the glucocorticosteroid and/or mineralo-corticosteroid receptors, particularly corticosteroid+addictive drug >addictive drug
2. Agonist of the glucocorticosteroid and/or mineralo-corticosteroid receptors, particularly corticosteroid>combination of agonist of the glucocorticbsteroid and/or mineralo-corticosteroid receptors, particularly corticosteroid+addictive drug
3. Agonist of the glucocorticosteroid and/or mineralo-corticosteroid receptors, particularly corticosteroid>addictive drug
4. Combination of agonist of the glucocorticosteroid and/or mineralo-corticosteroid receptors, particularly corticosteroid+addictive drug >addictive drug
5. Combination of agonist of the glucocorticosteroid and/or mineralo-corticosteroid receptors, particularly corticosteroid+addictive drug.

Using an established animal model, the use according to the invention and the pharmaceutical preparation according to the invention are explained in detail in the following:

Analyses in the animal model started with 96 male wistar-rats of which 77 animals finally were used in the relevant therapy experiments. The other animals had either died early or were used as untreated control for the subsequent neurobiological/neurochemical analyses. In the first phase of the experiment half of the animals were given the μ-agonist opioid etonitazen (ETZ) in their cages for free choice (four drinking solutions: water, 2 mg ETZ/l; 4 mg ETZ/l; 8 mg ETZ/l), the other half remained drug-naive and got water as the only drinking solution. After several weeks of adjusting, the rats developed a "controlled consumption", i.e. they drank—depending on the individual disposition and situational factors—more or less opiate; the dosage was, however, always moderate (mean value+/−standard deviation: 9.5+/−6.2 μg/kg/day).

The choice experiment was continued until the need for increase known from earlier experiments occurred prior to development of an addiction. During this period of time the animals that were later identified as addicted increased their opiate consume from one week to the next by four to eight times the amount of the original dosage. As soon as the need for an increase of dosage was observed, all animals of the relevant experiment were deprived of the opiate. At that time, the animals only got water as the only drinking solution. Two experiments were carried out sequentially and independently from each other with 48 animals each. In the first series, withdrawal started after 40 weeks, in the second series after 44 weeks.

After 15 weeks of abstinence (water as the sole drinking solution), all rats (i.e. also the drug naive animals) were subjected to a retest, wherein they had the choice between water and opiate solution (2 mg ETZ/l; 4 mg ETZ/l; 8 mg ETZ/l) for two weeks. For another two weeks, all the opiate solutions, however not the water offered additionally, were denatured with quinine hydrochloride (0.1 g/l) which is highly aversive for rats. Consequently, all the rats previously kept drug-naive (N=29) reduced their opiate intake, their average daily dosage was 6.2+/−0.2 µg/kg/day (here and in the following in each case mean value+/−SEM). With the drug-experienced animals two groups were clearly to be distinguished. One group took—despite denaturation—extremely high ETZ dosages (90.6+/−µg/kg/day, N=20), the other group reduced their opiate intake to a similar value as the drug-naive animals earlier (7.8+/−0.7 µg/kg/day, N=28). The first partial group was—in accordance with earlier results—classified as "addicted". All these animals, in contrast to the other rats which had not become addicted, demonstrated an increased need after the controlled substance consumption.

Once an opiate addiction has established in rats, it does not disappear spontaneously but continues to exist even after long periods of abstinence (Heyne, 1996). Untreated opiate-addicted animals remained addicts even after two further follow-up re-tests (7 and 16 weeks after end of the first retest). Under denaturation conditions, they drank 105.2+/−6.5 µg/kg/day on average. Animals which had not become addicted and previously drug-naive animals remained stable long-term, too. In the follow-up re-tests, they drank 6.6+/−0.5 and 6.5+/−0.6 µg/kg/day under denaturation conditions. The high doses taken by the addicted animals were not caused by a reduced aversion or even a preference for quinine, since both addicted and non-addicted animals avoided the quinine solutions when given the choice between water and solutions which were opiate-free and quinine-denaturated.

Two weeks after the end of the first re-test and 11 weeks after the end of the first re-test (i.e. two weeks after the end of the first follow-up re-test), treatment experiments were carried out. Three therapy concepts were tested:

(A) Ketamine pre-treatment for two weeks (an intraperitonal injection of 40 mg/kg S(+)-ketamin three times a week), immediately followed by forced administration of the opiate etonitazen via the drinking water (2 mg/l, mean daily dosage+/−SEM: 115+/−9 µg/kg/day) for a week.

(B) Forced treatment with corticosterone for two weeks. The only available drinking solution was a 259 mg/l corticosterone solution, the medium corticosterone daily dosage was 13.4+/−0.6 mg/kg/day.

(C) A combinatory, three-phase-treatment with corticosterone, followed by ETZ+corticosterone and finally ETZ. During the first week of therapy, the only drinking solution offered was a 250 mg/l corticosterone solution (daily dosage of corticosterone: 11.7+/−0.5 mg/kg/day). In the following week, the sole drinking solution contained 2 mg ETZ/l in addition to the corticosterone. The daily dosages were now 11.7+/−0.6 mg/kg/day for corticosterone and 93+/−5 µg/kg/day for ETZ. In the third week, the corticosterone was discontinued with, the drinking solution then only contained only 2 mg/l ETZ (daily dosage of ETZ: 109+/−5 µg/kg/day). Attention should be paid to the fact that the forced daily dosages are similar to those taken voluntarily by an addicted animal.

Treatment (A) and (B) did not show any effect. In the follow-up re-tests the addicted animals that had undergone such therapy still proved to be addicted, they did not differ from the untreated animals (110.4+/−6.6 µg/kg/day after treatment (A) and 100.1+/−6.3 µg/kg/day after treatment (B)). In contrast, treatment (C) was successful in all eight cases, where it was used with previously addicted rats. Under denaturation conditions, the relevant animals only drank 11.2+/−2.8 µg/kg/day of ETZ. Thus, they were cured from their addiction. The fact that this success of treatment not only was a temporary effect was confirmed in a follow-up test 11 weeks after treatment. The rats that were cured from their addiction after the three-phase-treatment turned out to be non-addicted in this test, too. Their intake values were 7.4+/−0.6 µg/kg/day and were, thus, not different to the ones of the rats which did not become addicted and of the previously drug-naive rats.

The treatment did not have any effect on any of the non-addicted-animals which did not demonstrate any changed intake behaviour—neither a spontaneous change nor a change caused by therapy. In the follow-up re-tests of the diverse groups, there were intake values of between 6.2+/−0.8 and 8.8+/−1.9 µg/kg/day; thus, the dosage was in the range of the first re-test. None of the non-addicted animals developed an addiction, none changed their intake behaviour after treatment.

Not only did the three-phase-treatment have a modulating influence—like anti-craving therapies—but it reversed the loss of control which had started earlier. This was possible neither with a corticosterone treatment nor with a forced administration of the addictive drug. Neither treatment (A) nor treatment (B) were successful despite the fact that they contained these treatment components. In this context, only an overlapping successive combination of both components lead to the desired result. All addicted rats treated according to the invention were cured, all addicted animals treated according to other therapy concepts or not treated at all remained addicts. It is to be assumed that with replication of the experiments including a higher number of subjects there might also be some "non-responders" but the complete success of this experiment leaves to expect that a very high percentage of subjects respond to this treatment.

REFERENCES

American Psychiatric Association (1994) Diagnostic and statistical manual of mental disorders (DSM IV), Washington D.C.

Brecht, J. G.; Poldrugb, F.; Schädlich, P. K. (1996) Die Krankheitskosten des Alkoholismus in der. Bundesrepublik Deutschland, PharmacoEconomics 10: 484-493

Bühringer, G.; Künzel, J.; Spies, G. (1997) Methadon-Substitution bei Opiatabhängigen, In: H. Watzl and B. Rockstroh (eds.), Abhängigkeit und Missbrauch von Alkohol und Drogen., Hogrefe Verlag, Gottingen, p. 249-264

Ehrenreich, H., Mangholz, A.; Schmitt, M.; Lieder, P.; Völkel, W.; Rüther, E.; Poser, W. (1997) OLITA: An alternative in the treatment of therapy-resistant chronic alcoholics. First evaluation of a new approach. Eur. Arch. Psychiatry Clin. Neurosci. 247: 51-54

Finkbeiner, T.; Rösinger, C.; Gastpar, M. (1996) Grundlagen und praktische Durchfuhrung der substitutionsgestützten Behandlung der Opiatabhängigkeit. In: K. Mann and G. Buchkremer (eds.) Such-Grundlagen-Diagnostik-Therapie. Gustav Fischer Verlag, Stuttgart, Jena, New York p. 303-316

Heyne, A. (1996) The development of opiate addiction in the rat. Pharmacol. Biochem. Behav. 53; 1-25

Küfner, H. (1997) Behandlungsfaktoren bei Alkohol- und Drogenabhängigen. In: H. Watzl and B. Rockstroh (eds.) Abhängigkeit und Missbrauch von Alkohol und Drogen. Hogrefe Verlag, Göttingen, p. 201-228

Küfner, H.; Feuerlein, W. (1989) In-patient treatment for alcoholism. A multi-center evaluation study,.Springer Verlag, Berlin Mann, K.; Mundle, G. (1996) Die pharmakologische Rückfallprophylaxe bei Alkoholabhängigen. Bedarf und Möglichkeiten. In: K. Mann and G. Buchkremer (eds.), Sucht-Grundlagen-Diagnostik-Therapie. Gustav Fischer Verlag, Stuttgart, Jena, New York, p. 317-322

Rist.F. (1996) Therapiestudien mit Alkoholabhängigen. In: K. Mann and G. Buchkremer (eds.) Such-Grundlagen-Diagnostik-Therapie. Gustav Fischer Verlag, Stuttgart, Jena, New York, p. 243-254

Roch, I.; Küfner, H.; Artz, J.; Böhmer, M.; Denis, A. (1992) Empirische Ergebnisse zum Therapieabbruch bei Drogenabhängigen: ein Literaturüberblick. Sucht 38: 305-322

Sass, H.; Soyka, M.; Mann, K.: Zieglgänsberger, W. (1996) Relapse Prevention in alcoholics with an anticraving drug treatment: first results of the Berlin study. Pharmacopsychiatry 27: 21-23

Schwoon, D. (1996) Nutzung professioneller Nachsorge und Selbsthilfegruppen durch Alkoholiker nach stationärer Kurzzeittherapie. In: K. Mann and G. Buchkremer (eds.) Sucht-Grundlagen-Diagnostik-Therapie. Gustav Fischer Verlag, Stuttgart, Jena, New York, p. 281-288

Sobell, L. C.; Sobell, M. B.; Toneatto, T.; Leo, G.I. (1993) What triggers the resolution of alcohol problems without treatment? Alcohol. Clin. Exp. Res. 17:217-224

Soyka, M. (1997) Neuere medikamentöse Ansätze in der Alkoholismustherapie. In: H. Watzl and B. Rockstroh (eds.) Abhängigkeit und Missbrauch von Alkohol und Drogen. Hogrefe Verlag, Göttingen, p. 229-247

Stetter, F.; Axmann-Kremar (1996) Psychotherapeutische Motivationsarbeit bei Alkoholkranken in der Entgiftungssphase. In: K. Mann and G. Buchkremer (eds.), Sucht-Grundlagen-Diagnostik-Therapie. Gustav Fischer Verlag, Stuttgart, Jena, New York, p. 255-264

Süß, H. M. (1995) Zur Wirksamkeit der Therapie bei Alkoholabhängigen: Ergebnisse einer Meta-Analyse. Psychol. Rundschau 46: 248-266

Veltrup, C.; Rohde, M.; Jacobi, M.; Koesters, C. (1995) Inanspruchnahme von Versorgungsangeboten durch Alkoholabhängige nach einer erweiterten Entzugsbehandlung. In: Ladewig, D. (ed.) Drogen und Alkohol Nr. 8 ISPA-PRESS, Lausanne, p. 133-149

Whitworth, A. B.; Fischer, E.; Lesch, O. M.; Nimmerrichter, A.; Oberbauer, H.; Platz, T.; Potgierer, A.; Walter, H.; Fleischhacker, C. (1996) Comparison of acamprosate and placebo in the long-term treatment of alcohol dependence. Lancet 347:1438-1442

Wieser, S.; Kunad, E. (1965) Katamnestische Studien beim chronischen Alkoholismus und zur Folge von Sozialprozessen bei Alkoholikern. Nervenarzt 36: 477-483

Wolffgramm, J. (1995) Abhängigkeitsentwicklung im Tiermodell. Z. Klin. Psychol. 24:107-117

Wolffgramm, J.; Heyne, A. (1995) From controlled drug intake to loss of control: the irreversible development of drug addiction in the rat. Behav. Brain Res. 70: 77-94

The invention claimed is:

1. A method of treating psychological dependency caused by an addictive drug in a human patient after a detoxification of a patient physically dependent on the addictive drug, of an addictive drug selected from the group consisting of an opiate and nicotine, comprising the step of administering to said patient a composition comprising:

a. at least one corticosteroid receptor agonist selected from the group consisting of cortisol, cortisone, cortisone acetate, corticosterone, prednisolone, prednisone, prednylidene, methylprednisolone, triamcinolone, betamethasone, dexamethasone, paramethasone, fluorcortolone, deflazacort, cloprednol and fludrocortisone; and b. the addictive drug;

wherein at least one corticosteroid receptor agonist is administered alone prior to a treatment with a composition of at least one corticosteroid receptor agonist and the addictive drug, followed by a forced administration of the addictive drug alone.

2. The method according to claim 1, wherein the corticosteroid receptor agonist is selected from the group consisting of dexamethasone, prednisolone and corticosterone.

3. The method according to claim 1, wherein the addictive drug is an opiate; wherein the addictive drug is administered in the amount of 5-100 mg/day; and wherein a maintenance dose of at least one corticosteroid receptor agonist is administered in the amount of 0.5-100 mg/day and 2 to 10 times higher amount for the initial dosage for a patient having a body weight of 60-80 kg.

* * * * *